June 5, 1956 W. R. SINGLETON Plant Pat. 1,481

CARNATION PLANT

Filed Sept. 6, 1955

WILLARD RALPH SINGLETON
*INVENTOR.*

*BY*
Roland A. Anderson
Attorney

United States Patent Office

Plant Pat. 1,481
Patented June 5, 1956

1,481

CARNATION PLANT

Willard Ralph Singleton, Suffolk County, N. Y., assignor to the United States of America as represented by the United States Atomic Energy Commission Application September 6, 1955, Serial No. 532,812

1 Claim. (Cl. 47—60)

This application relates to a new and distinct variety of carnation plant.

The White Sim variety of carnation is characterized by otherwise generally white flowers whose petals develop red sinus blotches often after the epidermal layer has been bruised. The present carnation is a mutant of the White Sim variety and does not have that fault. The White Sim carnation is an unpatented variety.

The present variety of carnation was developed by irradiating plants of the White Sim variety of carnation with gamma rays from a cobalt-60 source. The plant has been asexually reproduced through cuttings grown at the Brookhaven National Laboratory at Upton, New York. Two generations have been reproduced in this way and have bred true.

The plant is shown in the accompanying drawings, in which.

Figure 1:
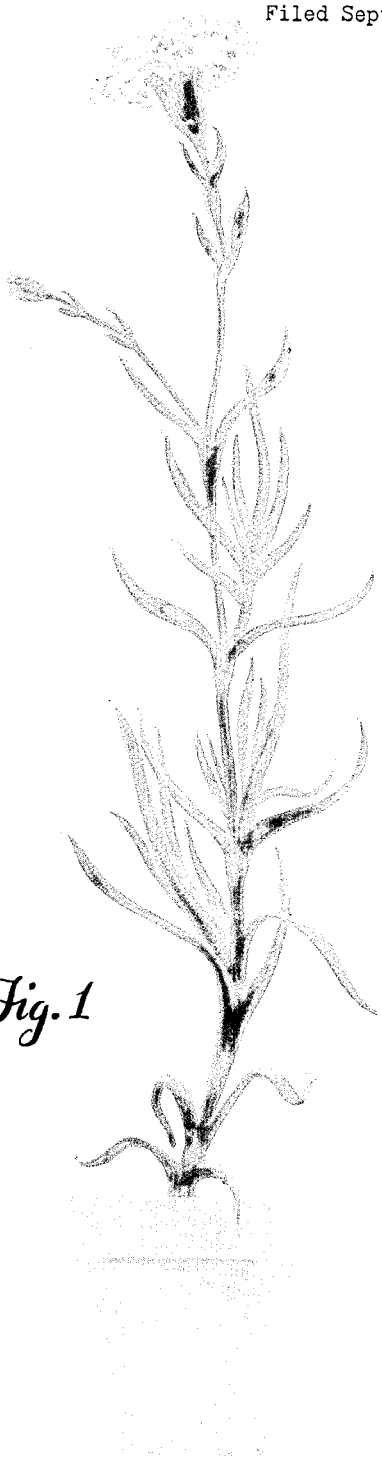
Figure 1 is a view of the entire plant showing its habit of growth.
Figure 2:
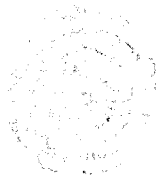
Figure 2 is a view of the flower produced by the plant.
Figure 3:
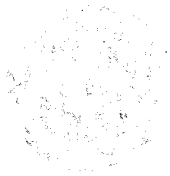
Figure 3 is a view for comparison of the flower of the parent White Sim variety of carnation showing the red sinus blotch.

The new plant is described as follows:

Parentage: White Sim variety of carnation.
Blooming habit: Continuous.

FLOWER

Bud:
- *Size.*—Large; similar to White Sim variety.
- *Form.*—Blunt conical.
- *Color.*—Glaucous green.
- *Sepals.*—United to form calyx.
- *Calyx.*—Firm, subcylindric.
- *Peduncle.*—Short.
- *Opening.*—Opens fully and readily.

Bloom:
- *Size.*—Large, of the order of 2½ to 3 inches.
- *Borne.*—Singly as grown commercially. Axillary buds usually removed to produce a single terminal flower.

- *Stem.*—Long, strong.
- *Form.*—Full, flat, slightly high center.
- *Petalage.*—Fully double. Approximately 50 petals per flower.
- *Color.*—Pure white.
- *Variegations.*—None.
- *Discolorations.*—None. Usual red sinus blotch of White Sim variety absent.

Petals:
- *Texture.*—Medium thick.
- *Appearance.*—Wavy.
- *Form.*—Obovate entire, slightly dentate.
- *Arrangement.*—Imbricated.
- *Persistence.*—Very persistent until flower withers. Do not drop.
- *Fragrance.*—Slight. Typical carnation odor.
- *Lastingness.*—On the plant, very long. As cut flower, very long.

Genital organs: Usually sterile.
- *Stamens, pollen, styles, stigmas.*—Absent.
- *Ovaries.*—Do not develop.

Fruit: None.

PLANT

Form: Shrub 1–3′ high. Stalks branched—generally with several in a clump.

Growth: Very vigorous, upright to sprawly if not staked. Compact, branching.

Foliage:
- *Leaflets.*—None.
- *Size.*—Medium to small.
- *Quantity.*—Abundant.
- *Color.*—Glaucous green, both upper and lower surfaces.
- *Shape.*—Lanceolate, almost grass-like.
- *Texture.*—Leathery, smooth.
- *Edge.*—Entire.
- *Serration.*—None.
- *Leaf stem.*—None. Leaves are sessile.
- *Stipules.*—Clasping the stalk.

Wood: Almost, but not truly woody. Herbaceous.
Thorns: Absent.

In general, it may be said that the plant I claim as new is similar to its parent except for the flower.

Having described and illustrated a new and distinct variety of carnation plant, I wish it to be understood that the distinctive feature I claim as new is as set forth in the appended claim.

I claim:

The new and distinct variety of carnation plant as herein described and illustrated, characterized particularly by its generally white flowers which are completely free of the red sinus blotch even when bruised characteristic of the white flowers of the variety "White Sim" (unpatented).

No references cited